United States Patent
Furukawa

(10) Patent No.: US 7,137,286 B2
(45) Date of Patent: Nov. 21, 2006

(54) GAS CHROMATOGRAPH SET

(75) Inventor: Masanao Furukawa, Osaka (JP)

(73) Assignee: Shimadzu Corporation (JP)

( * ) Notice: Subject to any disclaimer, the term of this patent is extended or adjusted under 35 U.S.C. 154(b) by 50 days.

(21) Appl. No.: 10/979,176

(22) Filed: Nov. 3, 2004

(65) Prior Publication Data
US 2005/0109079 A1    May 26, 2005

(30) Foreign Application Priority Data
Nov. 21, 2003  (JP) .............. 2003-391789

(51) Int. Cl.
*G01N 30/04* (2006.01)
(52) U.S. Cl. .............. 73/23.42; 73/23.35
(58) Field of Classification Search .......... 73/23.35, 73/23.41, 23.42
See application file for complete search history.

(56) References Cited
U.S. PATENT DOCUMENTS
4,474,889 A * 10/1984 Terry et al. .......... 436/161
6,447,581 B1 * 9/2002 Gellert et al. .......... 96/102

FOREIGN PATENT DOCUMENTS
JP    11-218528 A1    8/1999

* cited by examiner

Primary Examiner—Daniel S. Larkin
(74) Attorney, Agent, or Firm—Rader, Fishman & Grauer PLLC

(57) ABSTRACT

A gas chromatograph set of the present invention comprises a plurality of gas chromatographs and a flow passage assembly. Each of the gas chromatographs includes a column for separating sample-components, a carrier gas supply unit for supplying a carrier gas to the column and a detector for detecting eluted components from the column. The carrier gas supply unit comprises a carrier gas passage, and a flow controller unit for controlling a flow-rate that is connected to the carrier gas passage. The flow passage assembly comprises a metal plate inside which the carrier gas passages of the gas chromatographs are formed.

5 Claims, 4 Drawing Sheets

GAS CHROMATOGRAPH SET

BACKGROUND OF THE INVENTION

1. Field of the Invention

The present invention relates to a gas chromatograph used for measuring component concentrations in various samples.

2. Description of the Related Art

A gas chromatograph is provided with a column for separating sample components, a carrier gas supply unit for supplying carrier gas to the column and a detector for detecting eluted components from the column, and also has an injector for injecting a sample into the carrier gas, which is placed on the upstream side of the column.

A flow controller unit for controlling a flow rate, which includes a valve and a flow-rate sensor, is installed in the carrier gas supply unit so that a carrier gas, supplied from a carrier gas inlet, is supplied to a column from the valve through the flow-rate sensor.

With respect to the carrier gas supply unit, a structure in which a carrier gas passage is formed inside a metal substrate has been proposed (see Japanese Patent Application Laid-Open No. 11-218528). In this metal substrate, only one carrier gas passage is formed.

In the case of using a packed column in which a filler has been filled up as the column, since a bleeding component from the packed column is large, upon a temperature-rise analysis (that is, a method in which the temperature of the packed column raises during analysis), a base line on the chromatogram fluctuates largely, affecting adversely on a quantitative analysis. For this reason, generally, two of the same packed columns are installed, and these are connected to respective detectors. Then, the fluctuations in the base line are cancelled by obtaining a difference between detection outputs of these detectors.

The carrier gas has been supplied to each of the packed columns from each of the corresponding carrier gas supply units.

However, generally, a gas chromatograph has a column oven having a temperature ranging from room temperature to about 400° C. and a sample vaporization chamber having a temperature of about 250° C., together with heat-generating parts, such as a detector. Hence, there is a temperature difference of 2 to 3° C. between the carrier gas passages of the two carrier gas supply units.

It has generally been known that, even if the volume flow rate of gas is constant, there is a change of 0.6% in the mass flow rate when the surrounding temperature changes by 1° C. Moreover, the temperature coefficient of the flow-rate sensor is about 0.4%/° C. For this reason, a difference in a level of 2 to 3% occurs between the carrier-gas flow rates of the two carrier gas passages due to the above-mentioned temperature difference of 2 to 3° C. Consequently, base-line fluctuations occur in the chromatogram, resulting in adverse effect on the quantitative analysis.

There are differences among the flow rates of carrier gases, supplied from carrier gas passages made of a plurality of flow-passage assemblies to supply gases to a plurality of packed columns due to the above-mentioned temperature difference in the passage assemblies, resulting in a base-line shift of chromatogram that affects adversely on the quantitative analysis.

There have been demands for a constant carrier-gas flow rate not only in an attempt to cancel base-line fluctuations by obtaining a difference between a pair of detectors, but also in an attempt to use a plurality of gas chromatographs under the same conditions.

Moreover, there have been the same demands in capillary columns as in packed columns.

SUMMARY OF THE INVENTION

The objective of the present invention is to make carrier gas flow rates constant in a plurality of gas chromatographs.

A gas chromatograph set of the present invention comprises a plurality of gas chromatographs and a flow passage assembly. Each of the gas chromatographs includes a column for separating sample-components, a carrier gas supply unit for supplying a carrier gas to the column, and a detector for detecting eluted components from the column. Each carrier gas supply unit comprises a carrier gas passage and a flow controller unit for controlling a flow-rate that is connected to the carrier gas passage. The flow passage assembly comprises a metal plate inside where the carrier gas passages of the gas chromatographs are formed.

In the present invention, since a plurality of carrier gas passages are formed inside the commonly-used metal plate, it is possible to eliminate a temperature difference among the carrier gas passages, and consequently to eliminate a difference in the carrier gas flow rates among the gas chromatographs.

Since the flow passage assembly is shared, it becomes possible to cut costs.

With respect to the kinds of gas chromatograph to which the present invention is suitably applied, those which use a packed column in which the filler is filled up are proposed.

Moreover, with respect to the usage method of a gas chromatograph to which the present invention is suitably applied, a system in which two sets of gas chromatographs are installed to make a pair, with a sample is injected into one of the gas chromatographs so that a difference of detection signals between the two detectors can be obtained, is proposed. With this system, since a difference between detection signals from the detectors of the two gas chromatographs is obtained, it becomes possible to obtain a stable base line, and consequently to carry out an accurate quantitative analysis.

The foregoing and other objects, features, aspects and advantages of the present invention will become more apparent from the following detailed description of the present invention when taken in conjunction with the accompanying drawings.

BRIEF DESCRIPTIONS OF THE DRAWINGS

DESCRIPTION OF THE PREFERRED EMBODIMENTS

Figure 1:
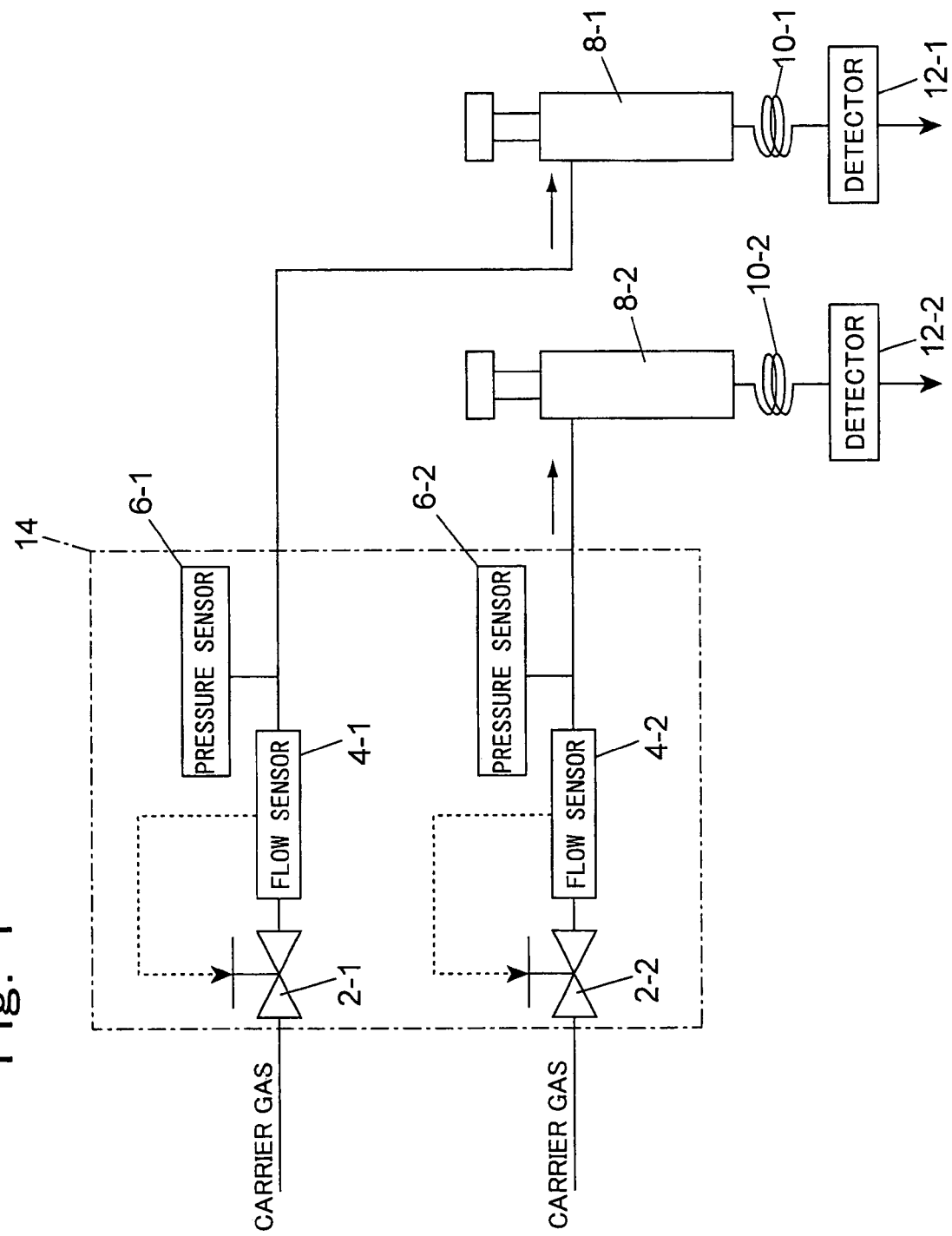
FIG. 1 is a flow passage drawing that schematically shows one embodiment.

FIG. 1 schematically shows one embodiment. Two sets of gas chromatographs are provided. In one of the gas chromatographs, a carrier gas supply unit, which supplies a carrier gas to a column 10-1 through an injection port 8-1, is provided with a valve 2-1 that is connected to a carrier gas inlet, a flow-rate sensor 4-1 placed on the downstream side of the valve 2-1 and a pressure sensor 6-1. The valve 2-1 is feed-back controlled based upon a detection signal from the flow-rate sensor 4-1 so as to fix the flow rate to a predetermined value.

The other gas chromatograph also has the same structure, and a carrier gas supply unit, which supplies a carrier gas to a column 10-2 through an injection port 8-2, is provided with a valve 2-2 that is connected to a carrier gas inlet, a flow-rate sensor 4-2 placed on the downstream side of the valve 2-2 and a pressure sensor 6-2. The valve 2-2 is also feed-back controlled based upon a detection signal from the flow-rate sensor 4-2 so as to fix the flow rate to a predetermined value.

Carrier gas passages of the two carrier gas supply units constitute a flow passage assembly 14 in which the respective carrier gas passages are formed inside of a common single substrate made of metal having superior heat conductivity. The valves 2-1 and 2-2, the flow-rate sensors 4-1 and 4-2 and the pressure sensors 6-1 and 6-2 are attached to the metal substrate of the flow passage assembly 14, and are respectively connected to the respective carrier gas passages.

Detectors 12-1 and 12-2, which respectively detect eluted components, are connected to the columns 10-1 and 10-2 on the downstream side.

A flow controller unit is constituted by valves 2-1 and 2-2 and flow-rate sensors 4-1 and 4-2.

In this gas chromatograph set, the two gas chromatographs may be used as independent gas chromatographs, respectively. Moreover, in the case of one of them being used as a reference system in an attempt to suppress fluctuations in the base line, a sample is injected into only one of the injection ports 8-1 and 8-2 so that a difference in the detection signals from the two detectors can be obtained.

Figure 2:
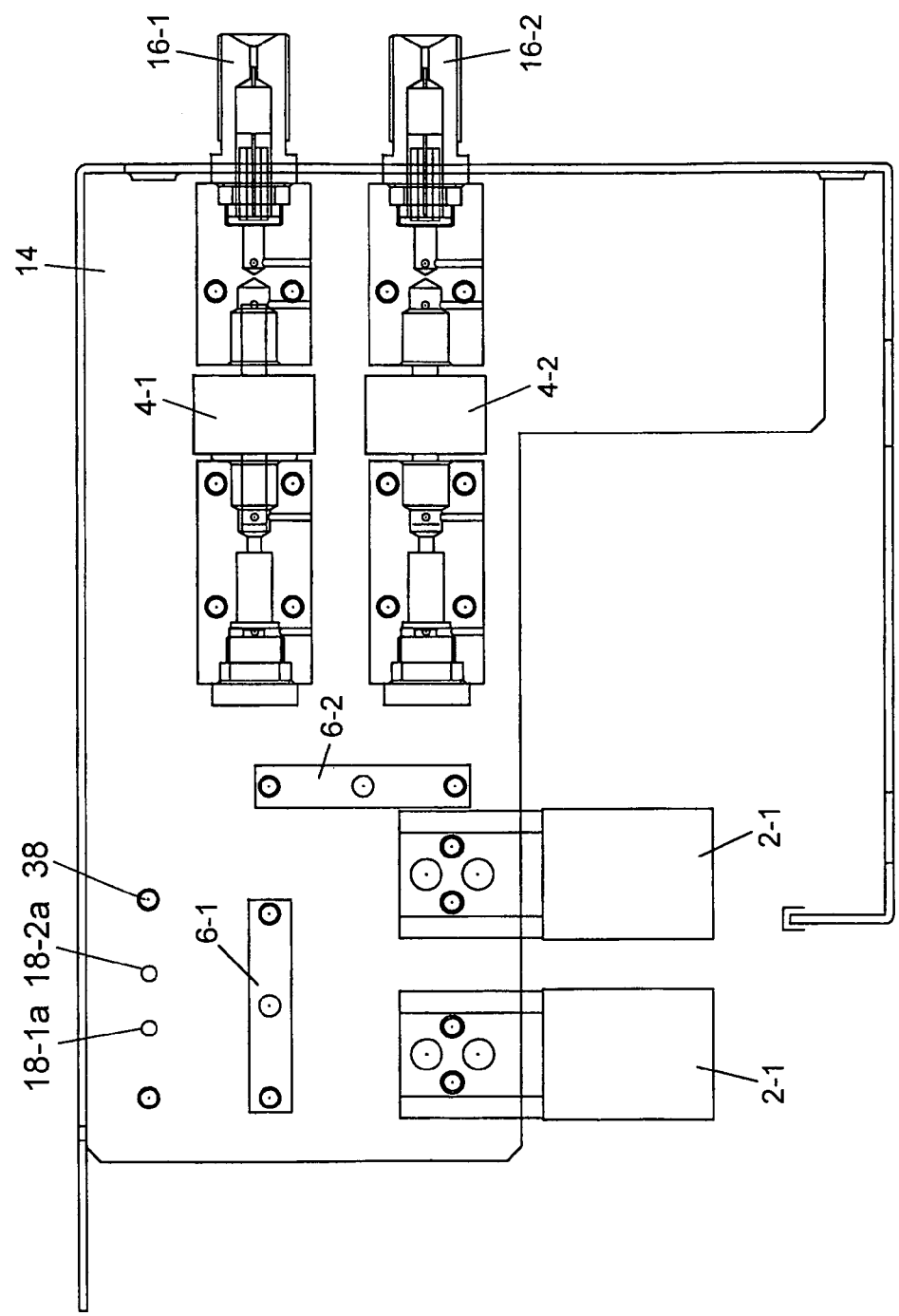
FIG. 2 is a plan view that shows a carrier gas supply unit in the embodiment.
Figure 3:
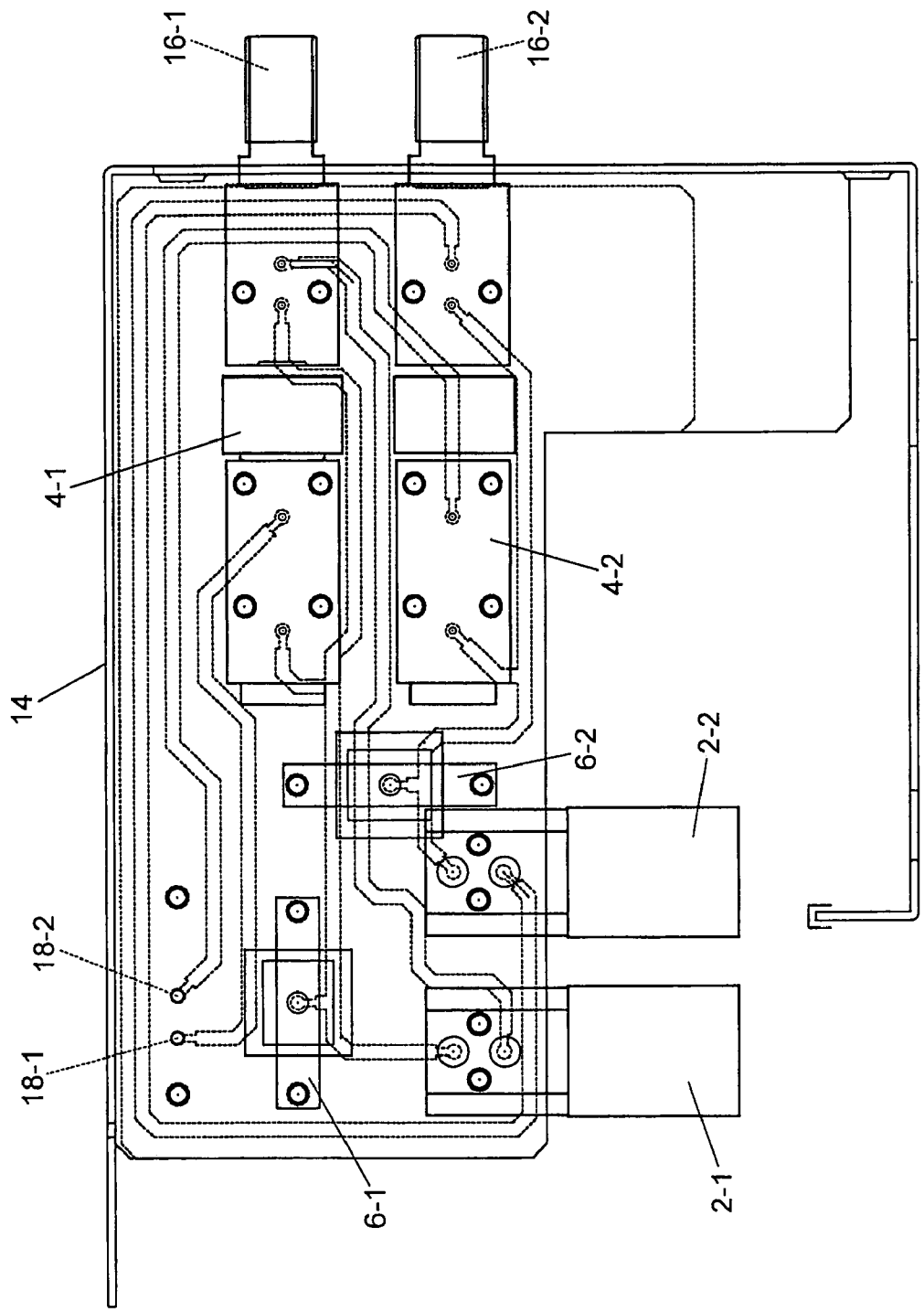
FIG. 3 is a plan view that shows a positional relationship between elements such as valves and flow passages inside a substrate in the carrier gas supply unit.
Figure 4:
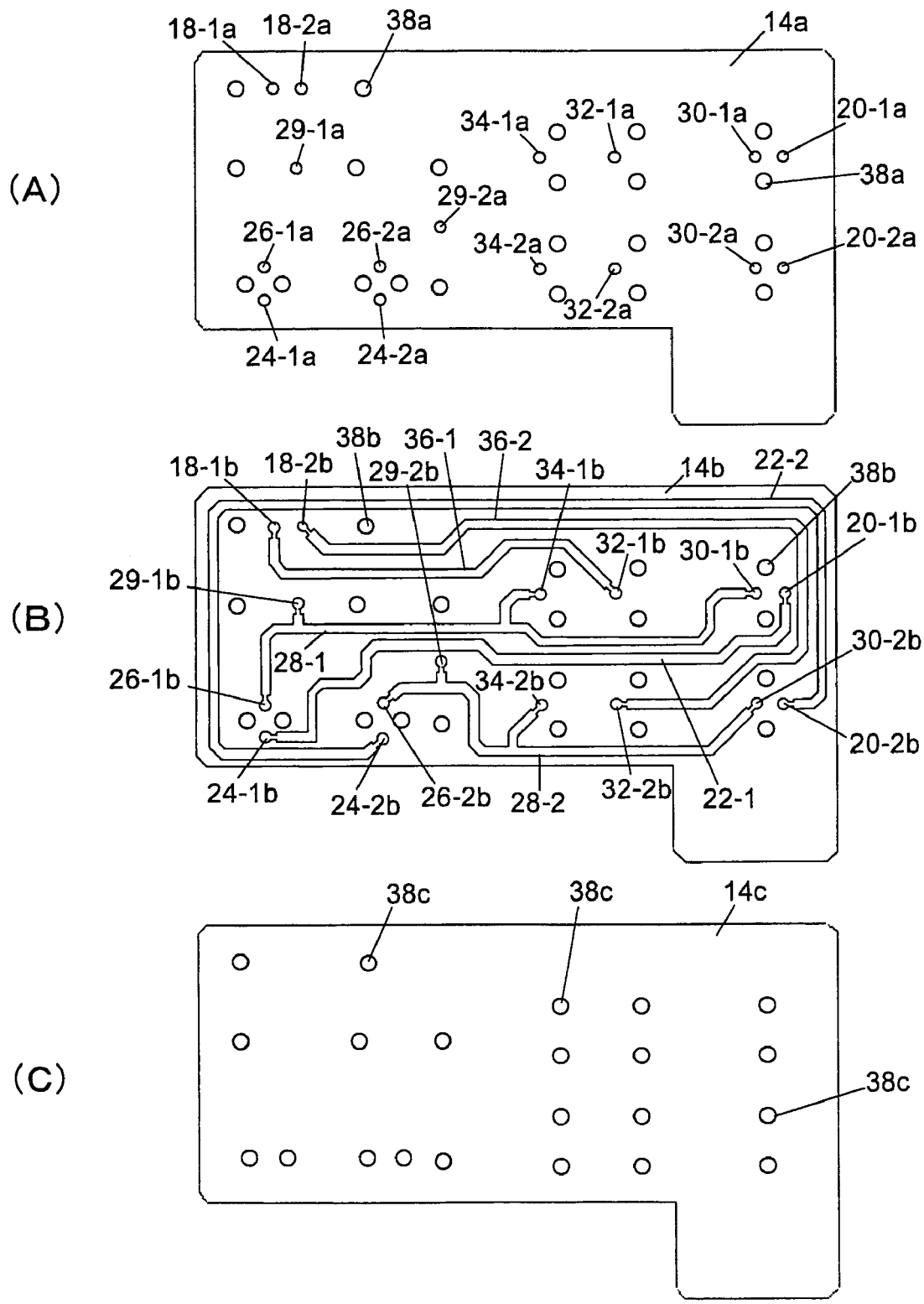
FIG. 4, consisting of FIGS. 4(A) to 4(C), is a plan view that shows a metal plate that forms a flow passage assembly in the carrier gas supply unit.

FIGS. 2 to 4 specifically show a carrier gas supply unit in this embodiment.

FIG. 2 is a plan view in which carrier gas inlet connectors 16-1 and 16-2, valves 2-1 and 2-2, flow-rate sensors 4-1 and 4-2 and pressure sensors 6-1 and 6-2 are placed and secured onto a metal substrate of the flow passage assembly 14. Reference numerals, 18-1*a* and 18-2*a*, respectively represent carrier gas outlets of the respective carrier gas supply units. Two holes 38, formed on both sides of each of alignments of the carrier gas outlets 18-1*a* and 18-2*a*, are used for securing a block (not shown) that introduces a carrier gas toward the downstream side.

As indicated by broken lines in FIG. 3, the carrier gas passages are formed inside the metal substrate of the flow passage assembly 14, and are connected to carrier gas inlet connectors 16-1 and 16-2, valves 2-1 and 2-2, flow-rate sensors 4-1 and 4-2 and pressure sensors 6-1 and 6-2 that are secured to the substrate, through inlet/outlet holes formed on the substrate surface. One of the carrier gas passages is connected to the carrier gas outlet 18-1 from the carrier gas inlet connector 16-1 through the flow-rate sensor 4-1 via the valve 2-1, and the pressure sensor 6-1 is connected to the carrier gas passage in the middle of the passage. In the same manner, the other carrier gas passage is connected to the carrier gas outlet 18-2 from the carrier gas inlet connector 16-2 passing through the flow-rate sensor 4-2 via the valve 2-2, and the pressure sensor 6-2 is connected to the carrier gas passage in the middle of the passage.

Referring to FIG. 4, the flow passage assembly 14 is explained.

The flow passage assembly is constituted by three metal plates, that is, an upper plate 14*a*, a middle plate 14*b* and a lower plate 14*c*, and is arranged so that the upper plate 14*a* is placed on the upper side and the lower plate 14*c* is placed on the lower side, with the middle plate 14*b* being placed in between; thus, these plates are integrally joined to one another.

The two carrier gas passages are formed in the middle plate 14*b* as grooves that penetrate the plate in the thickness direction. One of the carrier gas passages is provided with three flow passage grooves 22-1, 28-1 and 36-1. One end of the flow passage groove 22-1 forms an inlet hole 20-1*b*. The other end 24-1*b* of the flow passage groove 22-1 is adjacent to one end 26-1*b* of the flow passage groove 28-1, and the valve 2-1 is connected between the two ends 24-1*b* and 26-1*b*. The other end 30-1*b* of the flow passage groove 28-1 and an end 34-1*b* of a flow passage branched from the middle of the flow passage groove 28-1 are adjacent to one end 32-1*b* of the flow passage groove 36-1 so that the flow-rate sensor 4-1 is connected among the three ends 30-1*b*, 32-1*b* and 34-1*b*. The other end of the flow passage groove 36-1 serves as a carrier gas outlet 18-1*b*. The pressure sensor 6-1 is connected to a groove end 29-1*b* of a branched flow passage groove from the flow passage groove 28-1.

In the same manner, the other carrier gas passage is provided with three flow passage grooves 22-2, 28-2 and 36-2. One end of the flow passage groove 22-2 forms an inlet hole 20-2*b*. The other end 24-2*b* of the flow passage groove 22-2 is adjacent to one end 26-2*b* of the flow passage groove 28-2, and the valve 2-2 is connected to the two ends 24-2*b* and 26-2*b* in between. The other end 30-2*b* of the flow passage groove 28-2 and an end 34-2*b* of a flow passage branched from the middle of the flow passage groove 28-2 are adjacent to one end 32-2*b* of the flow passage groove 36-2 so that the flow-rate sensor 4-2 is connected among the three ends 30-2*b*, 32-2*b* and 34-2*b*. The other end of the flow passage groove 36-2 serves as a carrier gas outlet 18-2*b*. The pressure sensor 6-2 is connected to a groove end 29-2*b* of a branched flow passage groove from the flow passage groove 28-2.

The upper plate 14*a* to be superposed on the upper face of the middle plate 14*b* is provided with through holes 20-1*a*, 20-2*a*, 24-1*a*, 24-2*a*, 30-1*a*, 30-2*a*, 32-1*a*, 32-2*a*, 18-1*a*, 18-2*a*, 29-1*a*, 29-2*a*, 34-1*a* and 34-2*a* formed therein at positions that respectively correspond to the respective ends of the flow passage grooves in the middle plate 14*b*, that is, 20-1*b*, 20-2*b*, 24-1*b*, 24-2*b*, 30-1*b*, 30-2*b*, 32-1*b*, 32-2*b*, 18-1*b*, 18-2*b*, 29-1*b*, 29-2*b*, 34-1*b* and 34-2*b*, when the upper plate 14*a* is positioned on the middle plate 14*b* so as to be superposed thereon.

The lower plate 14*c* to be superposed on the lower face of the middle plate 14*b* is provided with no through holes at positions corresponding to the flow passage grooves of the middle plate 14*b* in a manner so as to close the lower face side of the flow passage grooves of the middle plate 14*b*.

The upper plate 14*a*, middle plate 14*b* and lower plate 14*c* are respectively provided with through holes 38*a*, 38*b* and 38*c* for attaching the inlet connectors 16-1 and 16-2, the valves 2-1 and 2-2, the flow-rate sensors 4-1 and 4-2, the pressure sensors 6-1 and 6-2, and a block used for directing carrier gases toward the downstream side (not shown in the Figure), and these through holes 38*a*, 38*b* and 38*c* are formed at positions that are made corresponding with one another when the upper plate 14*a*, the middle plate 14*b* and the lower plate 14*c* are positioned and respectively superposed.

The upper plate 14*a*, the middle plate 14*b* and the lower plate 14*c*, shown in FIG. 4, are positioned and superposed on one another, and joined to each other to form an integral substrate serving as the flow passage assembly 14 with flow passages formed therein, and the inlet connectors 16-1 and 16-2, the valves 2-1 and 2-2, the flow-rate sensors 4-1 and 4-2, and the pressure sensors 6-1 and 6-2 are then attached onto the upper plate 14*a*; thus, the carrier gas supply unit is formed.

In accordance with this carrier gas supply unit of the present embodiment, in the first carrier gas passage, carrier gas, directed through the carrier gas inlet 16-1, is directed to the valve 2-1 through the flow passage 22-1 inside the substrate of the flow passage assembly 14, and from the valve 2-1, the gas is again directed to the flow-rate sensor 4-1 through the flow passage 28-1 inside the substrate. The carrier gas that has passed through the flow-rate sensor 4-1 is again directed to the carrier gas outlet 18-1 through the flow passage 36-1 inside the substrate, and supplied to the injection port 8-1 therefrom. Moreover, the gas is also directed to the pressure sensor 6-1 from the middle point of the flow passage 28-1 so as to detect the pressure.

The second carrier gas passage also has the same structure, and carrier gas directed through the carrier gas inlet 16-2 is directed to the valve 2-2 through the flow passage 22-2 inside the substrate, and from the valve 2-2, the gas is again directed to the flow-rate sensor 4-2 through the flow passage 28-2 inside the substrate. The carrier gas that has passed through the flow-rate sensor 4-2 is again directed to the carrier gas outlet 18-2 through the flow passage 36-2 inside the substrate, and supplied to the injection port 8-2 therefrom. Moreover, the gas is also directed to the pressure sensor 6-2 from the middle point of the flow passage 28-2 so as to detect the pressure.

In the respective carrier gas passages, the flow rates are measured by the respective flow-rate sensors 4-1 and 4-2 so that the valves 2-1 and 2-2 are feed-back controlled so as to set predetermined flow rates.

Since the first and second carrier gas passages are formed inside the common metal substrate of the flow passage assembly 14, the two carrier gas passages are always maintained at the same temperature. Consequently, a sample is injected into the injection port of one of the gas chromatographs with the other chromatograph having no sample injected therein, and an analysis is carried out in this state so as to obtain a difference between the detectors of the two gas chromatographs; thus, it becomes possible to suppress fluctuations in the base line.

A method of manufacturing the flow passage assembly 14 will be described.

The metal plates 14*a*, 14*b* and 14*c* are made of metal having high thermal conductivity, and preferable material examples include stainless steel and iron, with a preferable thickness in a range of 0.2 to 1 mm.

Onto the metal plates 14*a*, 14*b* and 14*c*, the passage grooves and the through holes are formed through etching or stamping processes. The metal plates 14*a*, 14*b* and 14*c* are joined to one another through pressure welding. Specifically, the pressure welding refers to a process in which metal plates are pressed so as to be integrally welded by applying a pressure of about 10 MPa in a high-temperature atmosphere of no less than 800° C.

Although the embodiments have exemplified a structure in which carrier gas flow passages of two gas chromatographs are formed by a common flow passage assembly, carrier gas flow passages of three or more gas chromatographs may be formed by a common flow passage assembly.

The gas chromatograph of the present invention can be utilized to quantity-measure component concentrations in a sample in various fields, such as chemical, biochemical, environmental and medical fields.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A gas chromatograph set comprising:
   a plurality of gas chromatographs, each of which includes a column for separating sample-components, a carrier gas supply unit for supplying a carrier gas to the column, and a detector for detecting eluted components from the column;
   the carrier gas supply unit comprising a plurality of carrier gas passages, and a flow controller unit for controlling a flow-rate that is connected to each carrier gas passage; and
   a flow passage assembly having high thermal conductivity comprising an upper metal plate, a lower metal plate and a middle metal plate connected to and between the upper and lower metal plates to define from the of the plurality of the carrier gas passages,
   wherein the flow controller unit is attached to the upper metal plate of the flow passage assembly and
   wherein the middle plate is formed with a plurality of grooves and middle plate through holes, the upper plate is formed with a plurality of flow passage through holes and a plurality of upper plate through holes and the lower plate is formed with a plurality of lower plate through holes, the pluralities of upper plate through holes, middle plate through holes and lower plate through holes being in aligned registration with one another when the upper plate, middle plate and lower plate are connected together.

2. The gas chromatograph set according to claim 1, wherein each column is a packed column in which filler is filled up.

3. The gas chromatograph set according to claim 2, wherein the gas chromatographs make a pair, and
   the gas chromatograph set injects a sample into one of the gas chromatographs and obtains a difference of detection signals between the two detectors.

4. The gas chromatograph set according to claim 1, wherein the gas chromatographs make a pair, and
   the gas chromatograph set injects a sample into one of the gas chromatographs and obtains a difference of detection signals between the two detectors.

5. The gas chromatograph set according to claim 1, wherein each flow controller unit comprises a flow-rate sensor and a valve that is feed-back controlled so as to set the flow rate to a predetermined value based upon a detection signal of the flow-rate sensor.

* * * * *